US010932690B2

(12) United States Patent
Chiba

(10) Patent No.: US 10,932,690 B2
(45) Date of Patent: Mar. 2, 2021

(54) POSITION DETECTION SYSTEM AND OPERATION METHOD OF POSITION DETECTION SYSTEM

(71) Applicant: OLYMPUS CORPORATION, Tokyo (JP)

(72) Inventor: Atsushi Chiba, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 580 days.

(21) Appl. No.: 15/791,645

(22) Filed: Oct. 24, 2017

(65) Prior Publication Data
US 2018/0042519 A1 Feb. 15, 2018

Related U.S. Application Data

(63) Continuation of application No. PCT/JP2016/082088, filed on Oct. 28, 2016.

(30) Foreign Application Priority Data

Dec. 2, 2015 (JP) .............................. JP2015-236128

(51) Int. Cl.
*A61B 5/06* (2006.01)
*G01B 7/30* (2006.01)
*A61B 5/00* (2006.01)
(Continued)

(52) U.S. Cl.
CPC .......... *A61B 5/062* (2013.01); *A61B 1/00158* (2013.01); *A61B 1/041* (2013.01);
(Continued)

(58) Field of Classification Search
CPC ..... A61B 5/062; A61B 1/00158; A61B 1/041; A61B 1/6861; G01B 37/003; G01B 37/30
See application file for complete search history.

(56) References Cited

U.S. PATENT DOCUMENTS 6,493,573 B1 * 12/2002 Martinelli .............. A61B 90/36
128/899
8,556,802 B2 * 10/2013 Liu ..................... A61B 1/00158
600/103
(Continued)

FOREIGN PATENT DOCUMENTS

JP 2002000556 A 1/2002
JP 2006068501 A 3/2006
(Continued)

OTHER PUBLICATIONS

International Search Report dated Dec. 6, 2016 received in PCT/JP2016/082088.

*Primary Examiner* — Timothy J Neal
*Assistant Examiner* — Jae Woo
(74) *Attorney, Agent, or Firm* — Scully, Scott, Murphy & Presser, P.C.

(57) ABSTRACT

A position detection system includes: a detection target; detection coils each outputting a detection signal of strength of the alternating magnetic field; a guidance magnetic field generator including a magnetic field generation source, and a driving mechanism, wherein at least a part of the guidance magnetic field generator is formed of a conductor that generates an interference magnetic field; and a processor configured to: control an operation of the driving mechanism; calculate a correction value by using at least one of a position and a posture of the conductor; correct the measured value by using the correction value; and calculate at least one of a position and a posture of the detection target based on the corrected measured value.

9 Claims, 7 Drawing Sheets

(51) Int. Cl.
*A61B 1/00* (2006.01)
*G01B 7/00* (2006.01)
*A61B 1/04* (2006.01)

(52) U.S. Cl.
CPC ............ *A61B 5/6861* (2013.01); *G01B 7/003* (2013.01); *G01B 7/30* (2013.01)

(56) References Cited

U.S. PATENT DOCUMENTS

| | | | | |
|---|---|---|---|---|
| 9,766,093 | B2* | 9/2017 | Iida | A61B 1/041 |
| 2004/0207389 | A1 | 10/2004 | Nieminen et al. | |
| 2006/0209185 | A1* | 9/2006 | Yokoi | A61B 1/00016 |
| | | | | 348/65 |
| 2007/0078334 | A1* | 4/2007 | Scully | A61B 5/062 |
| | | | | 600/424 |
| 2007/0191671 | A1* | 8/2007 | Kawano | A61B 1/00036 |
| | | | | 600/12 |
| 2007/0221233 | A1* | 9/2007 | Kawano | A61B 1/00016 |
| | | | | 128/899 |
| 2008/0300458 | A1* | 12/2008 | Kim | A61B 1/00158 |
| | | | | 600/118 |
| 2010/0134096 | A1* | 6/2010 | Chiba | A61B 1/00158 |
| | | | | 324/207.22 |
| 2010/0204566 | A1* | 8/2010 | Uchiyama | A61B 1/00158 |
| | | | | 600/424 |
| 2011/0181273 | A1* | 7/2011 | Iida | A61B 1/00158 |
| | | | | 324/207.11 |
| 2011/0224537 | A1* | 9/2011 | Brunner | A61B 5/062 |
| | | | | 600/421 |
| 2017/0224423 | A1* | 8/2017 | Suzuki | A61B 1/041 |

FOREIGN PATENT DOCUMENTS

| | | |
|---|---|---|
| JP | 2006523473 A | 10/2006 |
| JP | 2008132047 A | 6/2008 |
| JP | 2009039356 A | 2/2009 |

* cited by examiner

POSITION DETECTION SYSTEM AND OPERATION METHOD OF POSITION DETECTION SYSTEM

CROSS-REFERENCE TO RELATED APPLICATION

This application is a continuation of PCT International Application No. PCT/JP2016/082088 filed on Oct. 28, 2016 which claims the benefit of priority from Japanese Patent Application No. 2015-236128 filed on Dec. 2, 2015, the entire contents of which are incorporated herein by reference.

BACKGROUND

The present disclosure relates to a position detection system and an operation method of the position detection system.

In recent years, a capsule medical apparatus introduced into a subject to acquire various types of information about the subject or to administer a drug to the subject has been developed. As an example, a capsule endoscope formed in a size which may be introduced into the gastrointestinal tract of a subject is known. The capsule endoscope has an imaging function and a wireless communication function inside a capsule-shaped casing, and after being swallowed into the subject, the capsule endoscope performs imaging while moving inside the gastrointestinal tract, and wirelessly transmits sequentially image data of images of the inside of an organ of the subject.

A system for performing position detection using such a capsule medical apparatus as a detection target has also been developed. For example, JP 2008-132047 A discloses a position detection system which includes a capsule medical apparatus having therein a magnetic field generating coil which generates a magnetic field for position detection by receiving power supply, and detection coils which detect the magnetic field generated by the magnetic field generating coil outside a subject, and performs calculation for detecting a position of the capsule medical apparatus based on the strength of the magnetic field detected by the detection coils.

In addition, a system for guiding a capsule medical apparatus introduced into a subject by a magnetic field has been proposed. For example, JP 2006-68501 A discloses a magnetic guidance medical system for guiding a capsule medical apparatus by introducing a capsule medical apparatus having therein a permanent magnet into a subject, providing a magnetic field generation unit outside the subject, and causing the magnetic field generation unit to move so as to change the magnetic field acting on the permanent magnet in the capsule medical apparatus.

SUMMARY

A position detection system according to one aspect of the present disclosure may include: a detection target including a magnetic field generator configured to generate an alternating magnetic field for position detection and a permanent magnet provided therein, the detection target being adapted to be introduced into a subject; a plurality of detection coils arranged outside the subject, each of the detection coils outputting a detection signal of strength of the alternating magnetic field; a guidance magnetic field generator including a magnetic field generation source configured to generate a guidance magnetic field for guiding the detection target, and a driving mechanism configured to change at least one of a position and a posture of the magnetic field generation source, wherein at least a part of the guidance magnetic field generator is formed of a conductor that generates an interference magnetic field by an action of the alternating magnetic field; a processor including hardware, wherein the processor is configured to: control an operation of the driving mechanism; calculate a correction value for correcting a measured value of the strength of the alternating magnetic field detected by each of the detection coils by using at least one of a position and a posture of the conductor; correct the measured value by using the correction value calculated by the correction value calculator; and calculate at least one of a position and a posture of the detection target based on the measured value corrected; wherein the processor calculates the correction value by further using at least one of latest position and posture of the calculated detection target.

The above and other features, advantages and technical and industrial significance of this disclosure will be better understood by reading the following detailed description of presently preferred embodiments of the disclosure, when considered in connection with the accompanying drawings.

DETAILED DESCRIPTION

Figure 1:
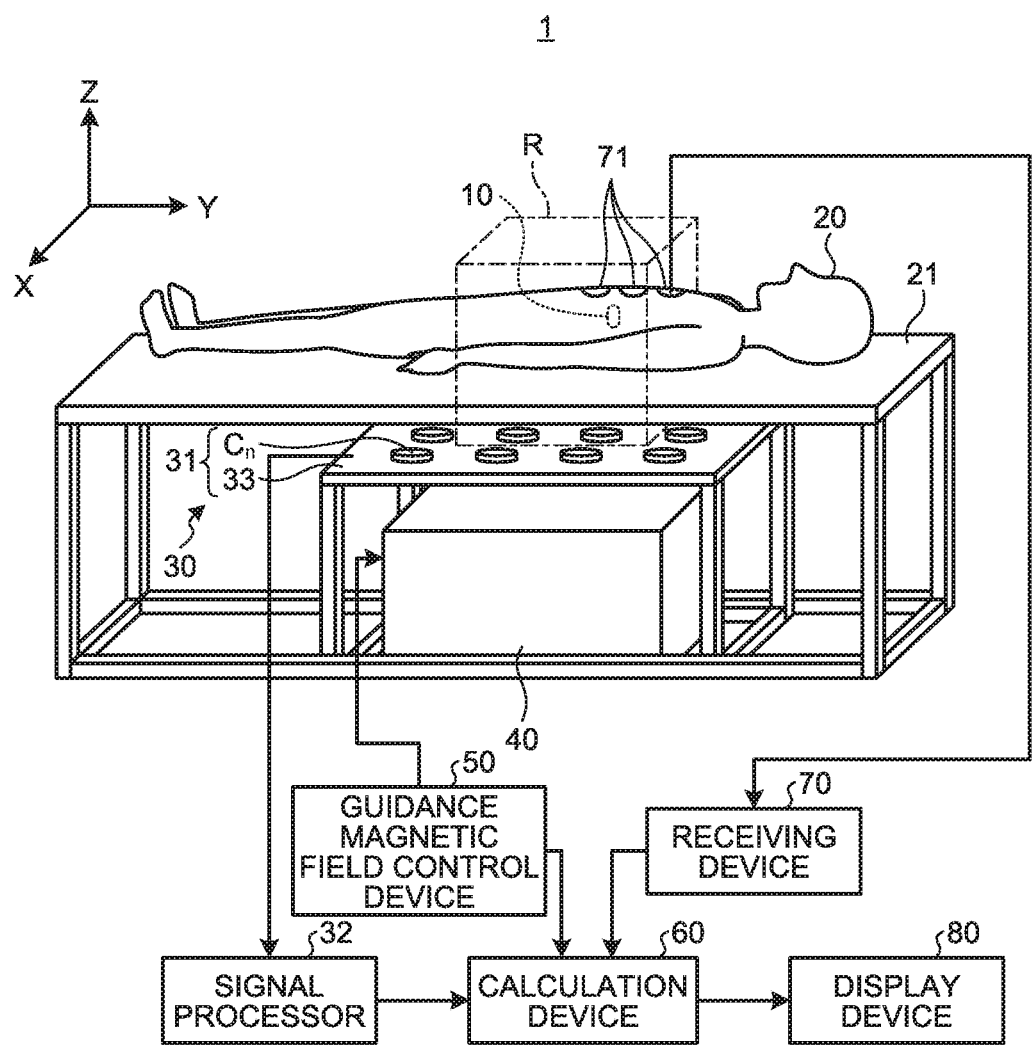
FIG. 1 is a schematic diagram illustrating an outline of a position detection system according to a first embodiment of the present disclosure.

Hereinafter, a position detection system and a position detection method according to embodiments of the present disclosure will be described with reference to the drawings. In the embodiments to be described below, as one form of a detection target of which a position and a posture are objects to be detected by the position detection system, a capsule endoscope is exemplified which is orally introduced into a subject and captures images of the inside of the gastrointestinal tract of the subject. However, the present disclosure is not limited by these embodiments. That is, the present disclosure may be applied to detection of positions and postures of various devices introduced into a subject, for example, a capsule endoscope which moves inside a lumen from the esophagus to the anus of the subject, a capsule medical apparatus which delivers a medicine or the like into the subject, a capsule medical apparatus which includes a pH sensor for measuring a pH in the subject.

In the following description, each figure only schematically illustrates a shape, a size, and a positional relationship to the extent that the contents of the present disclosure may be understood. Therefore, the present disclosure is not limited exclusively to the shape, the size, and the positional relationship exemplified in each figure. In the drawings, the same parts are denoted by the same reference signs.

First Embodiment

FIG. 1 is a schematic diagram illustrating an outline of a position detection system according to a first embodiment of the present disclosure. As illustrated in FIG. 1, a position detection system 1 according to the first embodiment is a system which detects a position of a capsule endoscope introduced into a subject 20 to capture an image of the inside of the subject 20, as an example of a detection target. The position detection system 1 includes a capsule endoscope 10, a bed 21, a magnetic field detection device 30, a guidance magnetic field generating device 40, a guidance magnetic field control device 50, a calculation device 60, a receiving device 70, and a display device 80. On the bed 21, the subject 20 is placed. The magnetic field detection device 30 detects a position-detecting magnetic field generated by the capsule endoscope 10. The guidance magnetic field generating device 40 generates a magnetic field for guiding the capsule endoscope 10. The guidance magnetic field control device 50 controls an operation of the guidance magnetic field generating device 40. The calculation device 60 performs a calculation process for detection of a position of the capsule endoscope 10 and the like based on a detection signal of the position-detecting magnetic field output from the magnetic field detection device 30. The receiving device 70 receives a signal wirelessly transmitted from the capsule endoscope 10 via a receiving antenna 71 affixed to the body surface of the subject 20. The display device 80 displays an image output from the calculation device 60 and positional information of the capsule endoscope 10, and the like.

Figure 2:
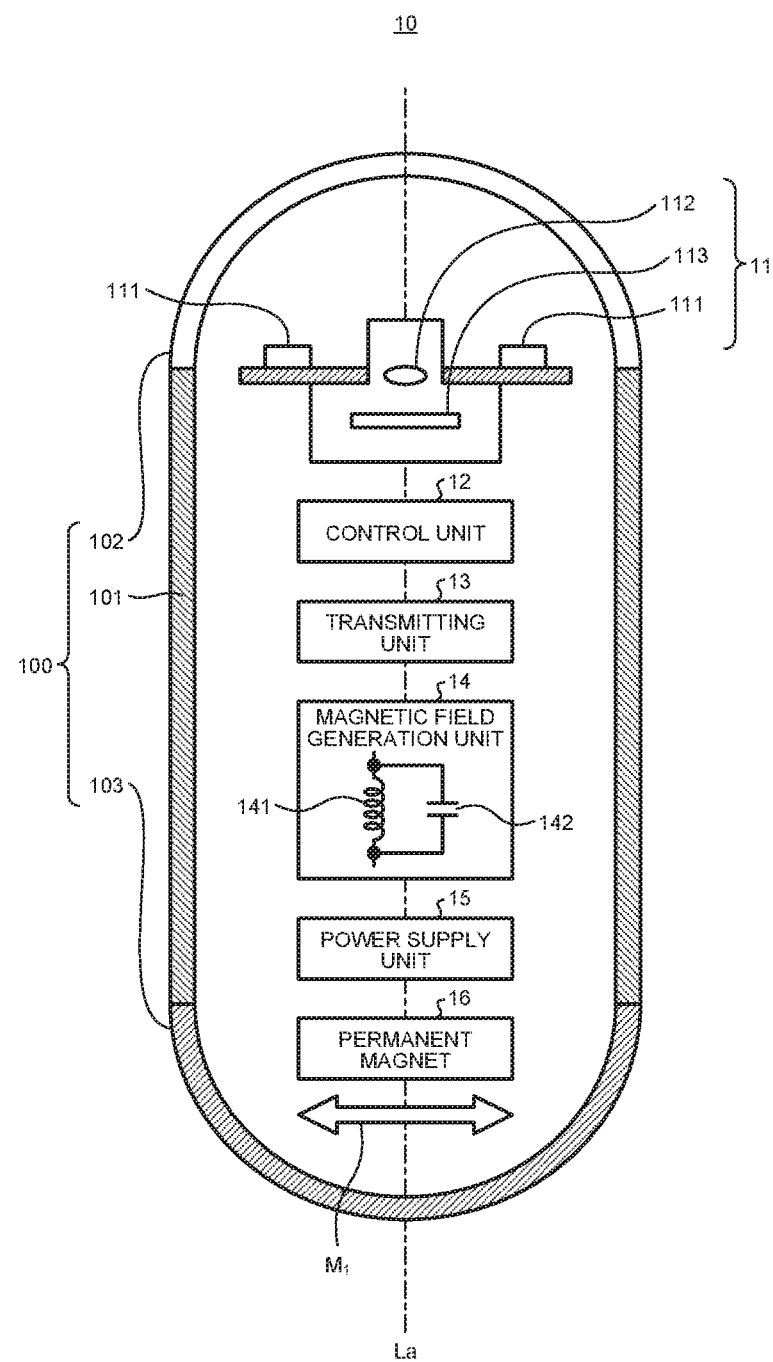
FIG. 2 is a schematic diagram illustrating an example of an internal structure of a capsule endoscope illustrated in FIG. 1.

FIG. 2 is a schematic diagram illustrating an example of an internal structure of the capsule endoscope 10 illustrated in FIG. 1. As illustrated in FIG. 2, the capsule endoscope 10 includes a casing 100, an imaging unit 11, a control unit 12, a transmitting unit 13, a magnetic field generation unit 14, a power supply unit 15, and a permanent magnet 16. The casing 100 is capsule-shaped and formed in a size easy to introduce into the subject 20. The imaging unit 11 is accommodated in the casing 100 and captures an image of the inside of the subject 20 to acquire an imaging signal. The control unit 12 controls an operation of each unit of the capsule endoscope 10 including the imaging unit 11, and performs a predetermined signal process to the imaging signal acquired by the imaging unit 11. The transmitting unit 13 wirelessly transmits the imaging signal which has been subjected to the signal process. The magnetic field generation unit 14 generates an alternating magnetic field as a position-detecting magnetic field of the capsule endoscope 10. The power supply unit 15 supplies power to each unit of the capsule endoscope 10.

The casing 100 is an outer casing formed in a size which may be introduced into an organ of the subject 20. The casing 100 has a cylindrical casing 101 having a cylindrical shape and two dome-shaped casings 102 and 103 having a dome shape and respectively closing open ends on both sides of the cylindrical casing 101. The cylindrical casing 101 is formed of a colored member which is substantially opaque to visible light. The dome-shaped casing 102 provided on a side of the imaging unit 11 is formed of an optical member which is transparent to light of a predetermined wavelength band such as visible light. The casing 100 includes the imaging unit 11, the control unit 12, the transmitting unit 13, the magnetic field generation unit 14, the power supply unit 15, and the permanent magnet 16 liquid-tightly. In FIG. 2, the imaging unit 11 is provided on a side of the dome-shaped casing 102 only, but the imaging unit 11 may be further provided on a side of the dome-shaped casing 103. In that case, the dome-shaped casing 103 is also formed of a transparent optical member.

The imaging unit 11 includes illumination units 111, an optical system 112, and an imaging element 113. Each illumination unit 111 has a light source such as an LED, and emits illumination light having a predetermined color component (for example, white light) in a region including an imaging view field of the imaging element 113 to illuminate the inside of the subject 20 through the dome-shaped casing 102. The optical system 112 has one or a plurality of lenses, and condenses light from the subject 20 onto a light-receiving surface of the imaging element 113 to form an image. The imaging element 113 has an image sensor such as a CMOS or a CCD, converts the light received on the light-receiving surface into an electrical signal, and outputs the electrical signal as an imaging signal.

The control unit 12 operates the imaging unit 11 at a predetermined imaging cycle and causes each illumination unit 111 to emit light in synchronization with the imaging cycle. In addition, the control unit 12 performs a predetermined signal process including A/D conversion on the imaging signal generated by the imaging unit 11 to generate image data.

The transmitting unit 13 includes a transmitting antenna. The transmitting unit 13 sequentially acquires the image data subjected to the signal process by the control unit 12 and related information to perform a modulation process, and wirelessly transmits sequentially the modulated signal to the outside via the transmitting antenna.

The magnetic field generation unit 14 includes a magnetic field generating coil 141 which generates a magnetic field by a flow of a current and a capacitor 142 which is connected in parallel with the magnetic field generating coil 141 and forms a resonance circuit together with the magnetic field generating coil 141. The magnetic field generation unit 14 receives power supply from the power supply unit 15 and generates an alternating magnetic field of a predetermined frequency as a position-detecting magnetic field.

The power supply unit 15 includes a power storage unit such as a button battery or a capacitor, and a switch unit such as a magnetic switch or an optical switch. When the power supply unit 15 is configured to have a magnetic switch, switching between ON and OFF states of power is performed by a magnetic field applied from the outside, and in the ON state, the power of the power storage unit is appropriately supplied to each component (the imaging unit 11, the control unit 12, and the transmitting unit 13) of the capsule endoscope 10, and in the OFF state, the supply is stopped.

The permanent magnet 16 is provided to enable the capsule endoscope 10 to be guided by a magnetic field applied from the outside. The permanent magnet 16 is fixedly disposed inside the casing 100 so that a magnetization direction intersects a major axis La of the casing 100. In the case illustrated in FIG. 2, the magnetization direction (an arrow $M_1$ in FIG. 2) of the permanent magnet 16 is orthogonal to the major axis La.

Figure 3:
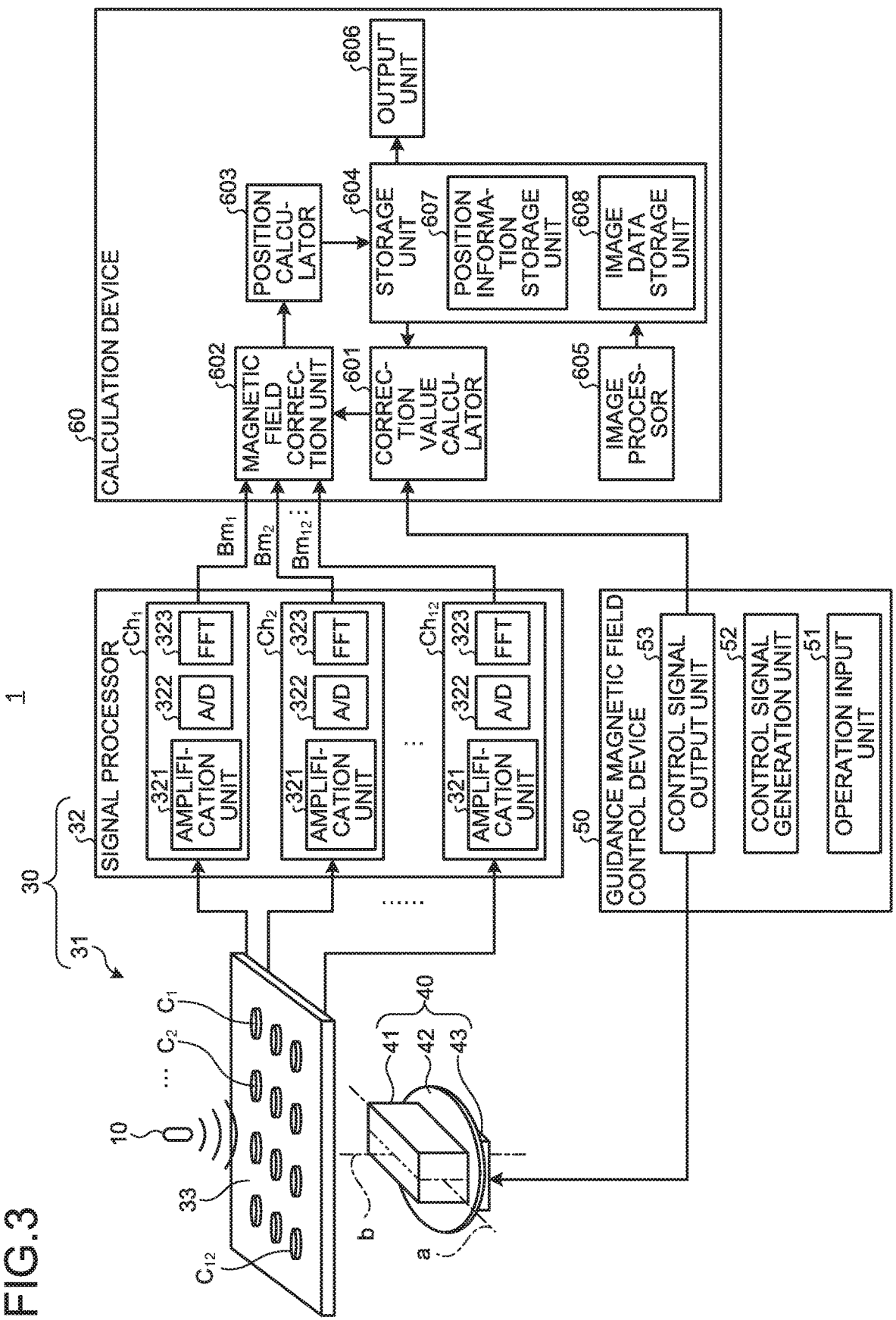
FIG. 3 is a diagram illustrating a detailed configuration of the position detection system illustrated in FIG. 1.

FIG. 3 is a diagram illustrating a detailed configuration of the position detection system 1 illustrated in FIG. 1. The magnetic field detection device 30 illustrated in FIG. 3 includes a coil unit 31, and a signal processor 32. In the coil unit 31, a plurality of detection coils $C_1$ to $C_{12}$ is arranged. The signal processor 32 processes detection signals respectively output from the detection coils $C_1$ to $C_{12}$.

The detection coils $C_n$ (n=1 to 12) are each obtained by winding a wire in a spiral shape, and its size is, for example, about 30 to 40 mm in opening diameter and about 5 mm in height. The detection coils $C_n$ are arranged on a main surface of a flat panel 33 formed of a nonmetallic material such as resin. In each of the detection coils $C_n$, a current corresponding to a change in the magnetic field at an arrangement position thereof is generated and output to the signal processor 32. In this sense, the current generated in each of the detection coils $C_n$ is nothing less than the detection signal.

The arrangement position and the number of the detection coils in the coil unit 31 are determined depending on a detection target region when detecting the capsule endoscope 10 in the subject 20 to be examined on the bed 21. The detection target region is set in advance depending on conditions such as a movable range of the capsule endoscope 10 and the strength of the position-detecting magnetic field generated by the capsule endoscope 10 in the subject 20 examined on the bed 21. For example, in the case illustrated in FIG. 1, a detection target region R is set as a three-dimensional region including a part of a region above the bed 21.

The signal processor 32 includes a plurality of signal processing channels $Ch_1$ to $Ch_{12}$, the signal processing channels $Ch_1$ to $Ch_{12}$ corresponding to the detection coils $C_1$ to $C_{12}$, respectively. The signal processing channels $Ch_n$ each include an amplification unit 321, an A/D converter (A/D) 322, and an FFT processor (FFT) 323. The amplification unit 321 amplifies a detection signal output from each of the detection coils $C_n$. The A/D converter (A/D) 322 digitally converts the amplified detection signal. The FFT processor (FFT) 323 performs a fast Fourier transform process on the digitally converted detection signal and outputs the detection signal to the calculation device 60.

The guidance magnetic field generating device 40 is disposed on an opposite side of the detection target region R for the capsule endoscope 10 with respect to the coil unit 31, that is, on a lower region side of the coil unit 31, and generates a guidance magnetic field for changing at least one of a position and a posture of the capsule endoscope 10 which has been introduced into the subject 20 on the bed 21. Here, the posture of the capsule endoscope 10 is represented by an elevation angle which is an angle with respect to a horizontal plane of the major axis La (see FIG. 2) of the capsule endoscope 10 with respect to the horizontal plane (XY plane) and a traverse angle (azimuth) of the major axis La rotating about an axis in a vertical direction (Z direction) from a predetermined reference position.

Figure 4:
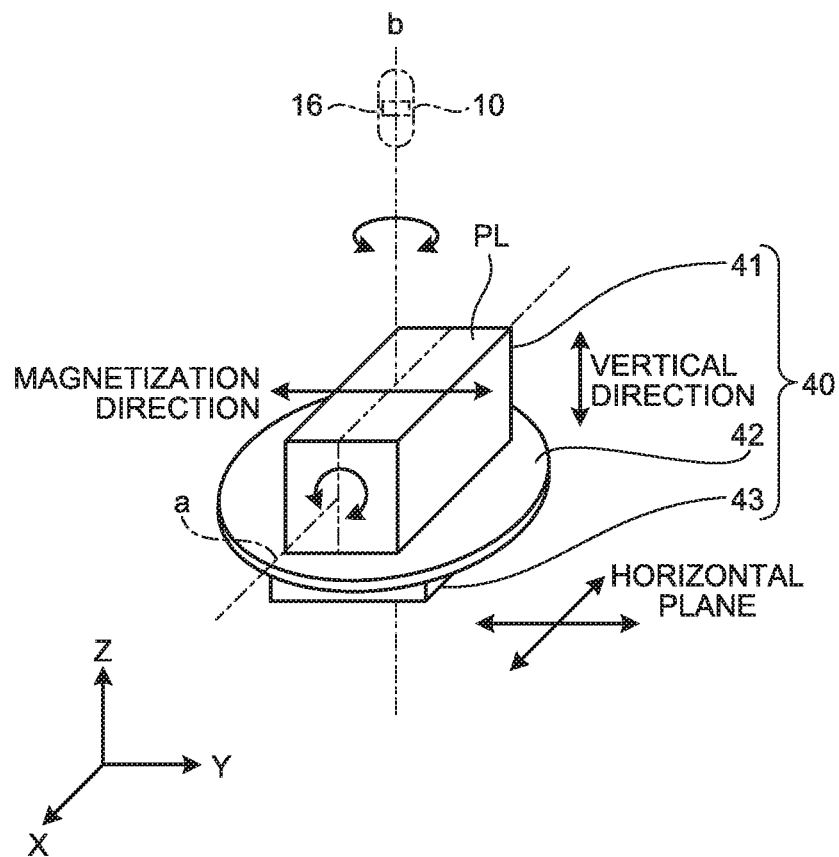
FIG. 4 is a schematic view illustrating a configuration example of a guidance magnetic field generating device illustrated in FIG. 3.

FIG. 4 is a schematic view illustrating a configuration example of the guidance magnetic field generating device 40. As illustrated in FIG. 4, the guidance magnetic field generating device 40 includes a permanent magnet (hereinafter referred to as an external permanent magnet) 41, a support member 42, and a magnet drive unit 43. The external permanent magnet 41 serves as a magnetic field generation source which generates the guidance magnetic field for the capsule endoscope 10. The support member 42 supports the external permanent magnet 41. The magnet drive unit 43 changes at least one of a position and a posture of the external permanent magnet 41 via the support member 42.

The guidance magnetic field generating device 40 is at least partially formed of a conductor. Generally, there exists the position-detecting magnetic field generated by the capsule endoscope 10 in a region where the guidance magnetic field generating device 40 is disposed. Consequently, by the position-detecting magnetic field changing with time, an eddy current flows through the conductor included in the guidance magnetic field generating device 40 and a new magnetic field (interference magnetic field) is generated. Therefore, the conductor included in the guidance magnetic field generating device 40 is a generation source of the interference magnetic field with respect to the position-detecting magnetic field. Since the conductor included in the guidance magnetic field generating device 40 moves and rotates under the control of the guidance magnetic field control device 50, the interference magnetic field also changes with time.

The external permanent magnet 41 is achieved by a bar magnet having a rectangular parallelepiped shape, for example. In that case, in an initial state, the external permanent magnet 41 is disposed so that one plane PL of four planes parallel to a magnetization direction thereof is parallel to the horizontal plane (see FIG. 4). Although the material of the external permanent magnet 41 is not particularly limited, for example, a metal magnet such as a neodymium magnet may be used. When a metal magnet is used as the external permanent magnet 41, the external permanent magnet 41 itself is a generation source of the interference magnetic field. Since the guidance magnetic field generated by the external permanent magnet 41 is stationary, the guidance magnetic field may be separated from the position-detecting magnetic field which is an alternating magnetic field.

The material of the support member 42 is not particularly limited, but when the support member 42 is formed of a conductor such as metal, the support member 42 may also be a generation source of the interference magnetic field.

The magnet drive unit 43 is a driving mechanism which changes a position and a posture of the external permanent magnet 41 via the support member 42. The magnet drive unit 43 includes a motor or the like which translates or rotates the external permanent magnet 41. Since a metal member is used in a commonly used motor, the magnet drive unit 43 may also be a generation source of the interference magnetic field with respect to the position-detecting magnetic field. When the support member 42 is formed of metal and the magnet drive unit 43 is covered by the support member 42 as seen from all the detection coils $C_1$ to $C_{12}$ as illustrated in FIG. 3, there is no need to consider the magnet drive unit 43 as a generation source of the interference magnetic field.

Figure 5:
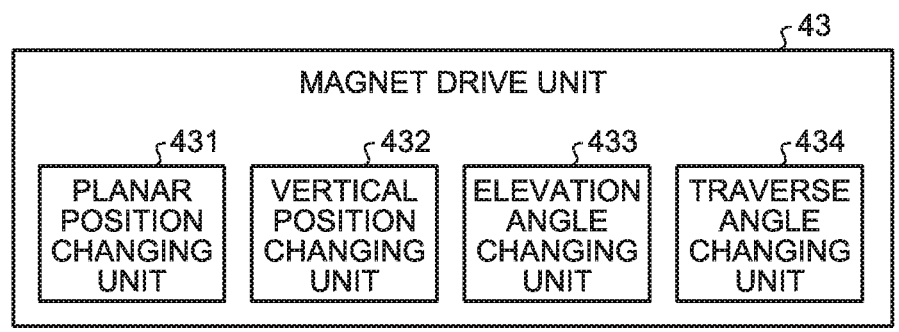
FIG. 5 is a block diagram illustrating a configuration example of a magnet drive unit illustrated in FIG. 4.

FIG. 5 is a block diagram illustrating a configuration example of the magnet drive unit 43. The magnet drive unit 43 includes a planar position changing unit 431, a vertical position changing unit 432, an elevation angle changing unit 433, and a traverse angle changing unit 434. The planar position changing unit 431 translates the external permanent magnet 41 in the horizontal plane. The vertical position changing unit 432 translates the external permanent magnet 41 in the vertical direction. The elevation angle changing unit 433 changes the elevation angle of the external permanent magnet 41 by rotating the external permanent magnet 41 about an axis which passes a center of the external permanent magnet 41, is orthogonal to the magnetization direction of the external permanent magnet 41 and is parallel to the horizontal plane. The traverse angle changing unit 434 changes the traverse angle of the external permanent magnet 41 by rotating the external permanent magnet 41 with respect to an axis in the vertical direction which passes the center of the external permanent magnet 41. Hereinafter, a rotation axis (an axis a illustrated in FIG. 4) used when the elevation angle changing unit 433 changes the elevation angle of the external permanent magnet 41 is referred to as a central axis a, and a rotation axis (an axis b illustrated in FIG. 4) used when the traverse angle changing unit 434 changes the traverse angle of the external permanent magnet 41 is referred to as a vertical axis b.

Through the operation of the magnet drive unit 43 described above, the external permanent magnet 41 and the support member 42 have five degrees of freedom: translation in a three-dimensional space, rotation about the central axis a, and rotation about the vertical axis b.

The guidance magnetic field control device 50 controls the guidance magnetic field generating device 40 in order to achieve guidance desired by a user with respect to the capsule endoscope 10. As illustrated in FIG. 3, the guidance magnetic field control device 50 includes an operation input unit 51, a control signal generation unit 52, and a control signal output unit 53. The operation input unit 51 is used by the user when guiding the capsule endoscope 10 introduced into the subject 20. The control signal generation unit 52 generates a control signal for the magnet drive unit 43 (driving mechanism) based on the operation to the operation input unit 51. The control signal output unit 53 outputs the control signal to the magnet drive unit 43 and the calculation device 60.

The operation input unit 51 includes an input device such as a joystick, an operation console including various buttons and switches, and a keyboard, and inputs, to the control signal generation unit 52, a signal corresponding to an operation performed from the outside. Specifically, the operation input unit 51 inputs, to the control signal generation unit 52, an operation signal for changing at least one of the position and the posture of the capsule endoscope 10 introduced into the subject 20 depending on an operation performed by the user.

The control signal generation unit 52 generates a control signal for controlling the magnet drive unit 43 of the guidance magnetic field generating device 40 depending on the operation signal input from the operation input unit 51.

The control signal output unit 53 outputs this control signal to the guidance magnetic field generating device 40 and to the calculation device 60.

When guiding the capsule endoscope 10, the magnet drive unit 43 is operated under the control of the guidance magnetic field control device 50, and thereby the external permanent magnet 41 is translated via the support member 42 in each of the horizontal plane and the vertical direction, and the elevation angle and the traverse angle are changed. The position and the posture of the capsule endoscope 10 change following the movement of the external permanent magnet 41.

The calculation device 60 executes a calculation process for calculating the position and the posture of the capsule endoscope 10 based on detection signals of the position-detecting magnetic field output from the signal processor 32 and a calculation process for generating an image of the inside of the subject 20 based on an image signal received via the receiving device 70. The calculation device 60 includes a correction value calculator 601, a magnetic field correction unit 602, a position calculator 603, a storage unit 604, an image processor 605, and an output unit 606. The correction value calculator 601 calculates a correction value for correcting an interference magnetic field with respect to the position-detecting magnetic field. The magnetic field correction unit 602 corrects a measured value of the strength of the position-detecting magnetic field detected by each of the detection coils $C_n$ by using the correction value calculated by the correction value calculator 601. The position calculator 603 calculates at least one of the position and the posture of the capsule endoscope 10 based on the corrected position-detecting magnetic field. The storage unit 604 stores various types of information used in the position detection system 1. The image processor 605 performs a predetermined image process to the received signal received by the receiving device 70, thereby generating image data of an image of the inside of the subject 20 captured by the capsule endoscope 10. The output unit 606 outputs the image of the inside of the subject 20 and various types of information such as the position and the posture of the capsule endoscope 10 to the display device 80.

The correction value calculator 601 calculates the strength of an interference magnetic field generated at the position of each of the detection coils $C_n$ depending on a relative relationship between at least one of the position and the posture of the capsule endoscope 10 and at least one of a position and a posture of the conductor included in the guidance magnetic field generating device 40, and outputs the strength of the interference magnetic field as a correction value for correcting the measured value of the strength of the position-detecting magnetic field.

The magnetic field correction unit 602 corrects the measured value of the strength of the position-detecting magnetic field detected by each of the detection coils $C_n$ by using the correction value calculated by the correction value calculator 601.

The position calculator 603 acquires the corrected strength of the position-detecting magnetic field at the position of each of the detection coils $C_n$ from the magnetic field correction unit 602, and calculates the current position and posture of the capsule endoscope 10 based on the strength.

The storage unit 604 includes a position information storage unit 607 and an image data storage unit 608. The position information storage unit 607 stores information indicating the position and the posture of the capsule endoscope 10 calculated by the position calculator 603. The image data storage unit 608 stores image data of an image generated by the image processor 605. Hereinafter, information indicating the position and the posture of the capsule endoscope 10 is also referred to as position information.

The storage unit 604 is achieved by using a ROM, a RAM, or the like. The storage unit 604 stores various control programs and various parameters for controlling each unit of the calculation device 60, a position detection calculation program for the capsule endoscope 10, an image processing program, and the like.

The calculation device 60 having the above configuration is configured, for example, by a computer such as a personal computer or a workstation including a general-purpose processor such as a CPU, a ROM, and a RAM.

The receiving device 70 selects, from a plurality of receiving antennas 71 to be affixed to the body surface of the subject 20 when the examination is performed by the capsule endoscope 10, a receiving antenna 71 having the highest received strength with respect to a radio signal transmitted from the capsule endoscope 10, and performs a demodulation process or the like to the radio signal received via the selected receiving antenna 71, thereby acquiring an image signal and related information.

The display device 80 includes various types of display such as a liquid crystal display and an organic EL display and displays information of an in-vivo image of the subject 20 and the position and the posture of the capsule endoscope 10 on a screen thereof based on the position information and the image data generated in the calculation device 60.

Figure 6:
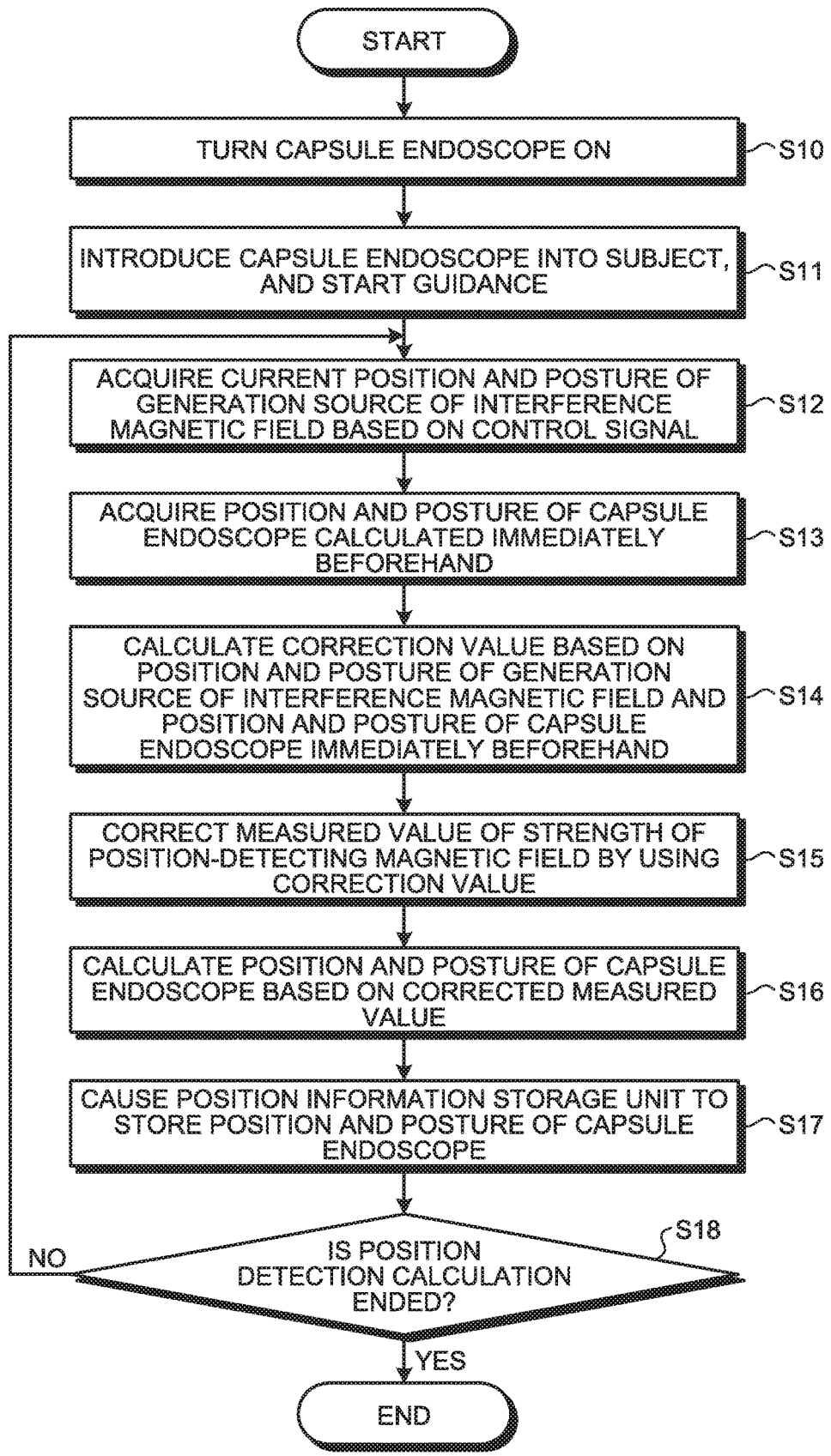
FIG. 6 is a flowchart illustrating a position detection method according to the first embodiment of the present disclosure.

Next, a position detection method according to the first embodiment will be described. FIG. 6 is a flowchart illustrating the position detection method performed by the position detection system 1.

First, in Step S10, the capsule endoscope 10 is turned on. As a result, power supply from the power supply unit 15 (see FIG. 2) to each unit of the capsule endoscope 10 is started, the imaging unit 11 starts imaging, and the magnetic field generation unit 14 starts generating the position-detecting magnetic field.

In the subsequent Step S11, the capsule endoscope 10 is introduced into the subject 20, and guidance to the capsule endoscope 10 is started. In detail, when the user operates the operation input unit 51 (see FIG. 3), the operation input unit 51 inputs an operation signal corresponding to the input operation to the control signal generation unit 52. In response to the operation signal, the control signal generation unit 52 generates a control signal for changing the position ($x_m$, $y_m$, $z_m$) and the posture (an elevation angle $\phi_m$, and a traverse angle $\theta_m$) in the three-dimensional space of the external permanent magnet 41. The control signal output unit 53 outputs the control signal to the magnet drive unit 43 and to the correction value calculator 601 of the calculation device 60.

In the subsequent Step S12, the correction value calculator 601 acquires a control signal for the guidance magnetic field generating device 40 from the guidance magnetic field control device 50, and based on this control signal, acquires current position and posture of the generation source of the interference magnetic field, that is, the conductor included in the guidance magnetic field generating device 40.

Hereinafter, the central position of the external permanent magnet 41 at time $t_i$ is represented by coordinates ($x_m(t_i)$, $y_m(t_i)$, $z_m(t_i)$), and the elevation angle and the traverse angle thereof are respectively represented by $\phi_m(t_i)$ and $\theta_m(t_i)$. The suffix i at the time $t_i$ represents the order of time of detection of the position-detecting magnetic field, and i=0, 1, 2, . . . . In the first embodiment, since the relative positional relationship between the external permanent magnet 41 and the conductor included in the guidance magnetic field generating device 40 is fixed, it is possible to acquire the position and the posture of the conductor, that is, a distribution of the generation source of the interference magnetic field in the three-dimensional space employing the position and the posture of the external permanent magnet 41 as reference.

In the subsequent Step S13, the correction value calculator 601 acquires from the position information storage unit 607 latest corrected position and posture of the capsule endoscope 10 calculated immediately beforehand by the position calculator 603. Hereinafter, the position and the posture of the capsule endoscope 10 at time $t_{i-1}$ are represented by coordinates ($x_c(t_{i-1})$, $y_c(t_{i-1})$, $z_c(t_{i-1})$), an elevation angle $\phi_c(t_{i-1})$, and a traverse angle $\theta_c(t_{i-1})$. When the position and the posture of the capsule endoscope 10 have not yet been calculated (that is, when i=0), the correction value calculator 601 may acquire, as data corresponding to the latest corrected position and posture of the capsule endoscope 10, the position and the posture of the capsule endoscope 10 at the time point, or may acquire preset initial values from the storage unit 604.

In the subsequent Step S14, the correction value calculator 601 calculates a correction value at the position of each detection coil $C_n$ based on the position and the posture of the generation source of the interference magnetic field acquired in Step S12 and the position and the posture of the capsule endoscope 10 acquired in Step S13.

The correction value may be calculated by, for example, the finite element method using a distribution of the position-detecting magnetic field based on the position and the posture of the capsule endoscope 10 and the position and the posture of the generation source of the interference magnetic field. Alternatively, the correction value may be acquired using a table in which the position and the posture of the capsule endoscope 10, the position and the posture of the generation source of the interference magnetic field, and the correction value at the position of each detection coil $C_n$ are associated with one another. In that case, the table is prepared by acquiring in advance the strength of the interference magnetic field depending on a relationship between the relative position and posture of the capsule endoscope 10 and those of the generation source of the interference magnetic field by simulation or the like, and stored in the storage unit 604.

In the subsequent Step S15, the magnetic field correction unit 602 corrects the measured value of the strength of the position-detecting magnetic field detected by each detection coil $C_n$, by using the correction value calculated in Step S14. A measured value (ideal value) $Bi_n$ of the strength of the magnetic field after correction at the time $t_i$ is given by the following formula (1), using a measured value $Bm_n$ of the strength of the position-detecting magnetic field detected at the time $t_i$ and strength $Bc_n$ of the interference magnetic field.

$$Bi_n = Bm_n - Bc_n \qquad (1)$$

In the subsequent Step S16, the position calculator 603 calculates the position and the posture of the capsule endoscope 10 based on the measured value corrected in Step S15. The position calculator 603 may calculate only one of the position and the posture of the capsule endoscope 10.

In the subsequent Step S17, the position calculator 603 causes the position information storage unit 607 to store the position and the posture of the capsule endoscope 10 calculated in Step S16.

In the subsequent Step S18, the calculation device 60 determines whether to end a position detection calculation for the capsule endoscope 10. Specifically, the calculation device 60 determines to end the position detection calculation when transmission of the wireless signal from the capsule endoscope 10 has been stopped, a case where a predetermined period of time has passed since the capsule endoscope 10 was turned on, or a case where an operation to end the operation of the calculation device 60 has been performed.

When the position detection calculation is not ended (Step S18: No), the process moves to Step S12. On the other hand, when the position detection calculation is ended (Step S18: Yes), the process is ended.

As described above, according to the first embodiment of the present disclosure, by forming, at least partially, the guidance magnetic field generating device 40 with a conductor, this conductor may be used as a generation source of a known interference magnetic field with respect to the position-detecting magnetic field. Therefore, even when the position and the posture of the generation source of the interference magnetic field change, by removing the influence of the interference magnetic field generated by the conductor included in the guidance magnetic field generating device 40 through calculation based on the position and the posture of the generation source of the interference magnetic field and the position and the posture of the capsule endoscope 10, accuracy of detecting the position and the posture of the capsule endoscope 10 may be improved.

Second Embodiment

Figure 7:
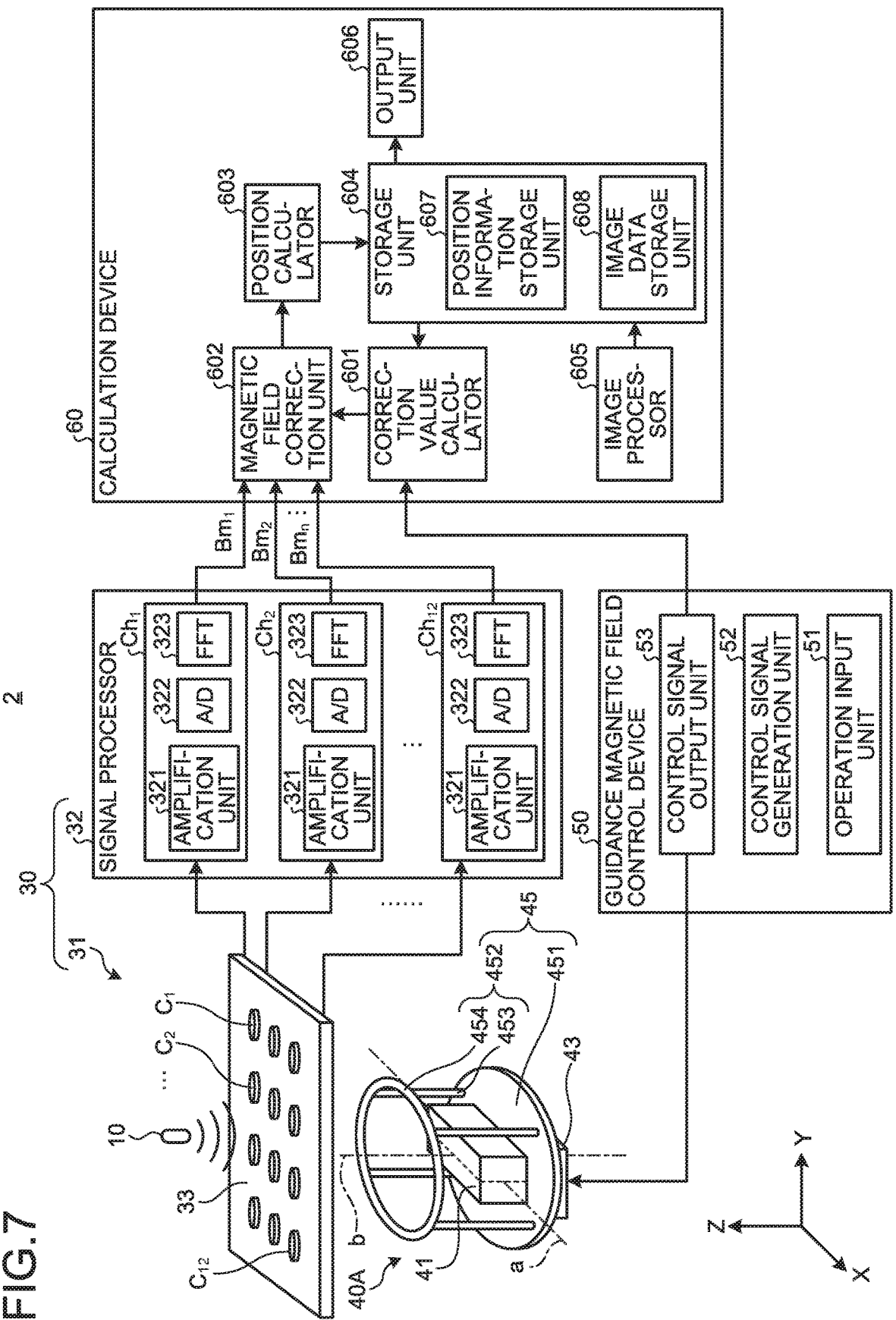
FIG. 7 is a diagram illustrating a configuration of a position detection system according to a second embodiment of the present disclosure.

Next, a second embodiment of the present disclosure will be described. FIG. 7 is a diagram illustrating a configuration of a position detection system according to the second embodiment of the present disclosure. The configuration of a position detection system 2 according to the second embodiment is similar to that in the first embodiment as a whole (see FIGS. 1 to 3), and the shape of a support member which supports an external permanent magnet 41 is different from that in the first embodiment.

As illustrated in FIG. 7, a guidance magnetic field generating device 40A according to the second embodiment includes a support member 45 which is capable of translating in a three-dimensional space and supports the external permanent magnet 41 rotatably about a central axis a and a vertical axis b. In FIG. 7, a rotation mechanism which rotates the external permanent magnet 41 in the support member 45 is omitted.

The support member 45 includes a disc-shaped plate material 451 and a frame 452 fixed to the plate material 451. The frame 452 has a plurality of (four in FIG. 7) support columns 453, each of the support columns 453 extending along a vertical direction, and an annular member 454 supported above the plate material 451 by these support columns 453. The whole support member 45 including the plate material 451 and the frame 452 is formed to be rotationally symmetric about a central axis in the vertical direction. In the case illustrated in FIG. 7, this central axis coincides with the vertical axis b.

The plate material 451 and the frame 452 are formed of a conductor such as metal. Therefore, the support member 45 may be a generation source of an interference magnetic field.

Since the frame 452 on an upper surface and side surfaces of the support member 45 does not cover the periphery of the external permanent magnet 41, a guidance magnetic field generated by the external permanent magnet 41 is not shielded by the support member 45, and is generated also in the detection target region R (see FIG. 1). Therefore, by translating the external permanent magnet 41 in the three-dimensional space via the support member 45 and by rotating the external permanent magnet 41 inside the support member 45, the capsule endoscope 10 may be guided by the guidance magnetic field.

The annular member 454 of the frame 452 is arranged so as to be located close to detection coils $C_n$ in comparison with the external permanent magnet 41. Accordingly, for the position-detecting magnetic field at the position of the detection coils $C_n$, the influence of the interference magnetic field by the frame 452 is dominant. Therefore, even if the external permanent magnet 41 rotates about the central axis a or the vertical axis b inside the frame 452, the rotation of the external permanent magnet 41 hardly affects detection signals output by the detection coils $C_n$.

Next, a position detection method according to the second embodiment will be described. The position detection method in the second embodiment is similar to that in the first embodiment as a whole (see FIG. 6), and details in the correction value calculation step in Step S14 are different from those in the first embodiment.

Figure 8:
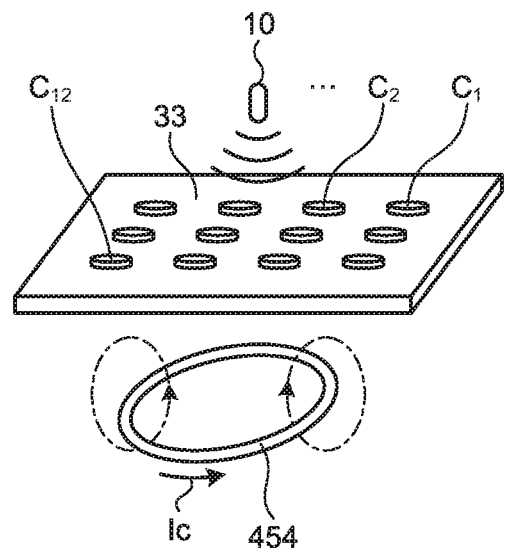
FIG. 8 is a schematic view for explaining a method for calculating correction values.

FIG. 8 is a schematic diagram for explaining a method of calculating a correction value. The annular member 454 of the support member 45 may be regarded as a loop coil. In that case, an induced current Ic generated in the annular member 454 by the position-detecting magnetic field generated from the capsule endoscope 10 passing through the opening of the annular member 454 is given by the following formula (2) by using resistance $R_{frame}$, an angular frequency $\omega$, and flux linkage $\phi$ of the annular member 454.

$$Ic = \frac{1}{R_{frame}} \omega \Phi \qquad (2)$$

By the induced current Ic, the interference magnetic field $Bc_n$ represented by the following formula (3) is generated at the position of the detection coils $C_n$. In the formula (3), a coefficient $K(r_n)$ is a distribution function of a magnetic field determined depending on a distance $r_n$ between the detection coils $C_n$ and the annular member 454.

$$Bc_n = K(r_n) \cdot Ic = \frac{K(r_n)}{R_{frame}} \cdot \omega \Phi \qquad (3)$$

Here, the position-detecting magnetic field generated from the capsule endoscope 10 may be regarded as a magnetic field generated by a magnetic dipole. Positional coordinates of the magnetic dipole and a magnetic moment of the magnetic dipole are indicated by (x, y, z) and (Mx, My, Mz), respectively, and a vector including these parameters is indicated by p=(x, y, z, Mx, My, Mz).

When the annular member 454 is regarded as a loop coil, if a position and an orientation of the loop coil are determined, a magnetic flux density $B_g(p)$ may be calculated with respect to a certain point of an opening plane of the loop coil. Since this calculation is performed for obtaining the electromotive force generated in the loop coil, an average value $B_{g\_mean}(p)$ of the magnetic flux density given by the following formula (4) is obtained. In the following formulas (4) to (6), arrows are attached to the magnetic flux density and vector elements such as the vector p.

$$\vec{B}_{g\_mean}(\vec{p}) = \frac{1}{N} \sum_{k=1}^{N} \vec{B}_g(\vec{p}_k) \qquad (4)$$

The right side of the formula (4) is an average of magnetic flux density $B_g(p_k)$ (k=1, . . . , N) in a vector $p_k$ including a position and a magnetic moment of the capsule endoscope 10.

The electromotive force generated in the loop coil is proportional to the winding number, the area, and the angular frequency of the loop coil with respect to the average value $B_{g\_mean}(p)$ of the magnetic flux density. When these proportionality coefficients are denoted by q, a current $I_c(p)$, which is given by dividing this electromotive force $q \cdot B_{g\_mean}(p)$ by an impedance $Z_{im}$ of the loop coil, flows to the loop coil as expressed by the following formula (5). The proportionality coefficient q is acquired in advance based on the diameter, the thickness, and the like of the annular member 454.

$$I_c(\vec{p}) = \frac{q \cdot \vec{B}_{g\_\text{mean}}(\vec{p})}{Z_{im}} \quad (5)$$

Considering the size of the annular member 454 regarded as a loop coil, it is possible to obtain a magnetic field generated from the loop coil by dividing the loop coil into a plurality of current elements and applying the Biot-Savart law thereto.

When a position vector of a current element is denoted by $r_c$, a current vector at each current element is denoted by $d_c$, and a position vector at a position where the magnetic field is detected is denoted by $r_s$, magnetic flux density $B_c(p)$ at the position where the detection is performed is given by the following formula (6).

$$\vec{B}_c(\vec{p}) = \oint \mu_0 \frac{I_c(\vec{p}) \cdot \vec{d}_c \times (\vec{r}_s - \vec{r}_c)}{4\pi |\vec{r}_s - \vec{r}_c|^3} \quad (6)$$

The calculation of the formula (6) is executed by using the vector p given based on position information of the capsule endoscope 10 at time $t_{i-1}$ and employing each point in the opening plane of the annular member 454 at the time $t_i$ as a current element. As the position vector $r_c$ of the current element, as an example, the sum of the coordinates of each point on the annular member 454 as viewed from the center point of the external permanent magnet 41 and the coordinates of the center point of the external permanent magnet 41 when the external permanent magnet 41 is moved by the magnet drive unit 43 in accordance with the control signal output from the guidance magnetic field control device 50 may be used.

The correction value calculator 601 calculates a magnitude of the magnetic flux density $B_c(p)$ given by the formula (6) as strength $Bc_n$ of the interference magnetic field, that is, a correction value.

As described above, according to the second embodiment of the present disclosure, since the conductor serving as the generation source of the interference magnetic field is intentionally disposed, it is possible to obtain the correction value through a calculation simpler than that in the first embodiment. In particular, by rotating the external permanent magnet 41 inside the support member 45, the need to consider the posture of the generation source of the interference magnetic field is eliminated, and it is sufficient to use only the position and the posture of the capsule endoscope 10 as well as the position of the generation source of the interference magnetic field. Consequently, it becomes possible to reduce a calculation load. Furthermore, by disposing the annular member 454 closer to the detection coils $C_n$ than the external permanent magnet 41, it becomes possible to easily calculate the interference magnetic field according to the Biot-Savart law.

Modification

Next, a modification of the second embodiment of the present disclosure will be described. When the capsule endoscope 10 is floating in liquid inside a subject 20 (see FIG. 1), as illustrated in FIG. 7, the capsule endoscope 10 is usually constrained by the guidance magnetic field vertically above the external permanent magnet 41, and moves following translational motion in a horizontal plane of the external permanent magnet 41. That is, the coordinates $(x_c, y_c)$ in the horizontal plane of the capsule endoscope 10 become substantially equal to the coordinates $(x_m, y_m)$ in the horizontal plane of the external permanent magnet 41, and in the horizontal plane, error in the position due to the influence of the interference magnetic field hardly occurs. Therefore, in that case, it is possible to calculate the correction value (strength of the interference magnetic field) while excluding the coordinates $(x_c, y_c)$ of the capsule endoscope 10 and the coordinates $(x_m, y_m)$ of the external permanent magnet 41 (See Step S14). That is, in that case, since the correction value may be calculated based only on the position and the posture in the vertical direction of the capsule endoscope 10 as well as the position in the vertical direction of the external permanent magnet 41, it becomes possible to greatly reduce the calculation load.

Third Embodiment

Figure 9:
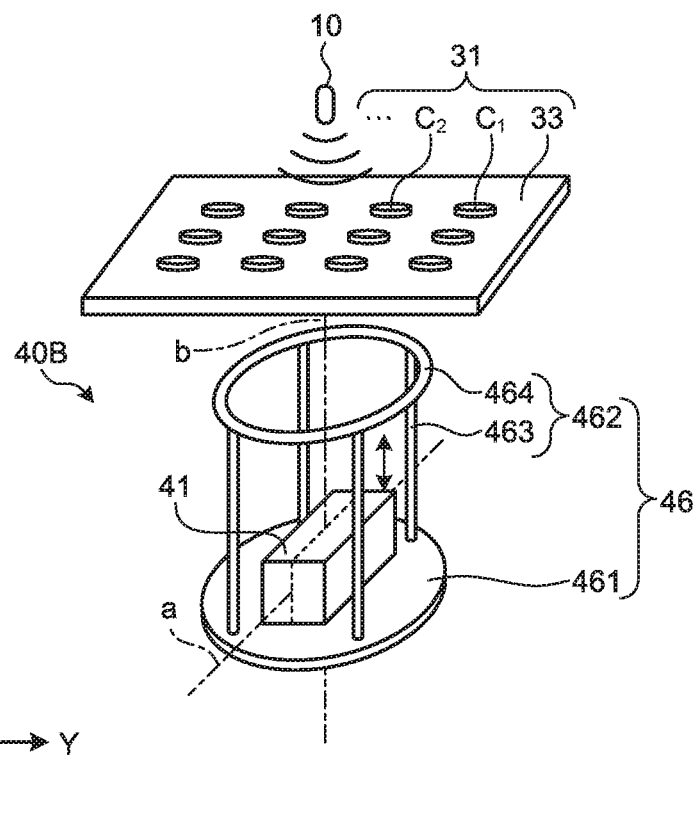
FIG. 9 is a schematic view illustrating a partial configuration of a position detection system according to a third embodiment of the present disclosure.

Next, a third embodiment of the present disclosure will be described. FIG. 9 is a schematic view illustrating a partial configuration of a position detection system according to the third embodiment of the present disclosure. The configuration of the position detection system according to the third embodiment is similar to that in the first embodiment as a whole (see FIGS. 1 to 3), and the shape of a support member which supports an external permanent magnet 41 is different from that in the first embodiment.

As illustrated in FIG. 9, a guidance magnetic field generating device 40B according to the third embodiment includes a support member 46 which is capable of translating in a horizontal plane and supports the external permanent magnet 41 rotatably about a central axis a and a vertical axis b and translatably in a vertical direction. In FIG. 9, a rotating mechanism which rotates the external permanent magnet 41 and a moving mechanism which moves the external permanent magnet 41 in the vertical direction in the support member 46 are omitted.

As with the case of the support member 45 illustrated in FIG. 7, the support member 46 includes a disc-shaped plate material 461 and a frame 462 fixed to the plate material 461, and is formed to be rotationally symmetric about a central axis in the vertical direction. The frame 462 has a plurality of (four in FIG. 9) support columns 463, each of the support columns 463 extending along the vertical direction, and an annular member 464 supported above the plate material 461 by these support columns 463. The length of each of the support columns 463 is longer than that of the support columns 453 illustrated in FIG. 7, and the external permanent magnet 41 may move in the vertical direction within a range of the length of the support columns 463. The annular member 464 is arranged so as to be located close to detection coils $C_n$ in comparison with the external permanent magnet 41.

The plate material 461 and the frame 462 are formed of a conductor such as metal. Therefore, the support member 46 may be a generation source of an interference magnetic field.

In the third embodiment, the support member 46 is translated only in the horizontal plane while the height in the vertical direction is fixed. Consequently, the annular member 464, which is the generation source of the interference magnetic field which has a dominant influence on a position-detecting magnetic field at the positions of the plurality of detection coils $C_n$, has a constant height. Therefore, even if the external permanent magnet 41 moves in the vertical direction, or rotates about the central axis a or the vertical axis b inside the support member 46, the movement and the rotation of the external permanent magnet 41 hardly affect detection signals output from the plurality of detection coils $C_n$.

As described above, according to third embodiment of the present disclosure, since the support member 46 is used, the need to consider the position and the posture in the vertical direction of the generation source of the interference magnetic field is eliminated when calculating the correction value in Step S14 of FIG. 6. Consequently, it becomes possible to further reduce a calculation load in comparison with the second embodiment.

Modification

Next, a modification of the third embodiment of the present disclosure will be described. As described above, when the capsule endoscope 10 is floating in liquid in a subject 20 (see FIG. 1), the capsule endoscope 10 is usually constrained by a guidance magnetic field vertically above the external permanent magnet 41, and moves following translational motion of the external permanent magnet 41 in the horizontal plane. Consequently, error in the position due to the influence of the interference magnetic field hardly occurs in the horizontal plane. Therefore, in comparison with the third embodiment, it is possible to calculate the correction value (strength of the interference magnetic field) while further excluding the coordinates $(x_m, y_m)$ in the horizontal plane of the external permanent magnet 41 (the support member 46). That is, it is possible to calculate the correction value only with the position and the posture of the capsule endoscope 10.

The first to third embodiments of the present disclosure described above and the variations thereof are merely examples for carrying out the present disclosure, and the present disclosure is not limited thereto. In addition, the present disclosure may make various disclosures by appropriately combining a plurality of constituent elements disclosed in the above-mentioned first to third embodiments and the variations thereof. It is obvious from the above description that the present disclosure may be variously modified in accordance with specifications and the like, and that various other embodiments are possible within the scope of the present disclosure.

According to the present disclosure, since a guidance magnetic field generating device is at least partially formed of a conductor, and a measured value of the strength of a position-detecting magnetic field is corrected by using correction values based on at least one of a position and a posture of the conductor, it is possible to accurately detect a position and a posture of a detection target based on the position-detecting magnetic field generated by the detection target even when a position or a posture of a generation source of an interference magnetic field changes.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A position detection system comprising:
    a detection target including a magnetic field generator configured to generate an alternating magnetic field for position detection, the detection target further having a permanent magnet provided therein, the detection target being configured to be introduced into a subject;
    a plurality of detection coils arranged outside the subject, each of the plurality of detection coils outputting a detection signal of strength of the alternating magnetic field;
    a guidance magnetic field generator comprising:
        a magnetic field generation source configured to generate a guidance magnetic field for guiding the detection target, and
        a driving mechanism configured to change at least one of a position and a posture of the magnetic field generation source,
        wherein at least a part of the guidance magnetic field generator is formed of a conducting material that is provided in the magnetic field generation source and generates an interference magnetic field by an action of the alternating magnetic field;
    one or more processors, each comprising hardware, wherein the one or more processors are configured to:
        control an operation of the driving mechanism;
        calculate a correction value for correcting a measured value of the strength of the alternating magnetic field detected by each of the plurality of detection coils by using at least one of a position and a posture of the conducting material, the position and the posture being changed by the driving mechanism;
        correct the measured value by using the calculated correction value; and
        calculate at least one of a position and a posture of the detection target based on the corrected measured value;
    wherein the one or more processors calculate the correction value by further using at least one of a latest position and posture of the detection target;
    the guidance magnetic field generator further includes a support member configured to support the magnetic field generation source,
    the support member comprises the conducting material that generates the interference magnetic field by the action of the alternating magnetic field, and
    the drive mechanism is configured to rotate the support member about two axes orthogonal to each other, and translate the support member in a three-dimensional space to change the at least one of the position and the posture of the magnetic field generation source.

2. The position detection system according to claim 1, wherein the one or more processors acquire at least one of the position and the posture of the conducting material based on a control signal of the driving mechanism.

3. The position detection system according to claim 1, wherein
    a portion of the support member is located closer to the plurality of detection coils than the magnetic field generation source, and
    wherein the one or more processors calculate the correction value by using the latest position and posture of the detection target and the position of the support member.

4. The position detection system according to claim 3, wherein the one or more processors calculate the correction value by using a position in a vertical direction and a posture of the detection target and a position in the vertical direction of the support member.

5. The position detection system according to claim 3, wherein the portion of the support member located closer to the plurality of detection coils than the magnetic field generation source has an annular shape.

6. The position detection system according to claim 1, wherein the support member is translated by the driving mechanism in a two-dimensional plane, together with the magnetic field generation source while a height in a vertical direction is fixed,
wherein a portion of the support member is located closer to the plurality of detection coils than the magnetic field generation source, and
wherein the one or more processors calculate the correction value by using the latest position and posture of the detection target and the position of the support member in a two-dimensional plane excluding the vertical direction.

7. The position detection system according to claim 6, wherein the one or more processors calculate the correction value by using a position and a posture of the detection target.

8. The position detection system according to claim 1, wherein the detection target is a capsule endoscope including an image sensor configured to generate an image signal by capturing an image of the inside of the subject.

9. An operation method of a position detection system that detects a position of a detection target including a magnetic field generator configured to generate an alternating magnetic field for position detection and a permanent magnet provided in the detection target, the detection target being configured to be introduced into a subject, wherein the position detection system includes:
　a plurality of detection coils arranged outside the subject, each of the plurality of detection coils outputting a detection signal of strength of the alternating magnetic field; and
　a guidance magnetic field generator comprising:
　　a magnetic field generation source configured to generate a guidance magnetic field for guiding the detection target, and
　　a driving mechanism configured to change at least one of a position and a posture of the magnetic field generation source,
　　wherein at least a part of the guidance magnetic field generator is formed of a conducting material that is provided in the magnetic field generation source and generates an interference magnetic field by an action of the alternating magnetic field;
　one or more processors, each comprising hardware, wherein the one or more processors are configured to:
　　calculate a correction value for correcting a measured value of the strength of the alternating magnetic field detected by each of the plurality of detection coils;
　　correct the measured value; and
　　calculate at least one of a position and a posture of the detection target,
　wherein the guidance magnetic field generator further includes a support member configured to support the magnetic field generation source,
　the support member comprises the conducting material that generates the interference magnetic field by the action of the alternating magnetic field, and
　the drive mechanism is configured to rotate the support member about two axes orthogonal to each other, and translate the support member in a three-dimensional space to change the at least one of the position and the posture of the magnetic field generation source;
the operation method comprising:
calculating a correction value for correcting the measured value of the strength of the alternating magnetic field detected by each of the plurality of detection coils by using at least one of a position and a posture of the conducting material, the position and the posture being changed by the driving mechanism;
correcting the measured value by using the correction value; and
calculating at least one of a position and a posture of the detection target based on the measured value, wherein
the one or more processors calculate, in the calculating the correction value, the calculation value by further using at least one of latest position and posture of the detection target.

* * * * *